(12) United States Patent
Meruva et al.

(10) Patent No.: US 10,317,359 B2
(45) Date of Patent: Jun. 11, 2019

(54) DIFFERENTIAL CARBON DIOXIDE SENSOR

(71) Applicants: Ravi Kumar Meruva, Lexington, MA (US); Kalachar Haranahalli Chadimane Byrappachar, Arasikere (IN); Nagabhushanam Gonuguntla, Tadimarri (IN); Srirama Kumar Kasi, Katrenikona Mandal (IN)

(72) Inventors: Ravi Kumar Meruva, Lexington, MA (US); Kalachar Haranahalli Chadimane Byrappachar, Arasikere (IN); Nagabhushanam Gonuguntla, Tadimarri (IN); Srirama Kumar Kasi, Katrenikona Mandal (IN)

( * ) Notice: Subject to any disclaimer, the term of this patent is extended or adjusted under 35 U.S.C. 154(b) by 207 days.

(21) Appl. No.: 15/399,032

(22) Filed: Jan. 5, 2017

(65) Prior Publication Data

US 2017/0191954 A1    Jul. 6, 2017

Related U.S. Application Data

(60) Provisional application No. 62/274,988, filed on Jan. 5, 2016.

(51) Int. Cl.
    *G01N 27/27*    (2006.01)
    *G01N 27/30*    (2006.01)
    *G01N 27/333*   (2006.01)

(52) U.S. Cl.
    CPC .......... *G01N 27/27* (2013.01); *G01N 27/302* (2013.01); *G01N 27/333* (2013.01)

(58) Field of Classification Search
    CPC .. G01N 33/492; G01N 33/4925; G01N 27/27; G01N 27/302; G01N 27/333; A61B 5/14542; A61B 5/14551–14556
    See application file for complete search history.

(56) References Cited

U.S. PATENT DOCUMENTS 4,452,682 A * 6/1984 Takata ................. G01N 33/492
                                              204/400
4,810,351 A * 3/1989 Chapoteau ......... G01N 27/3335
                                              204/418

(Continued)

FOREIGN PATENT DOCUMENTS

EP    0475692 A1    3/1992
EP    2727597 A1    5/2014

(Continued)

*Primary Examiner* — Gurpreet Kaur
(74) *Attorney, Agent, or Firm* — Lambert Shortell & Connaughton; Gary E. Lambert; David J. Connaughton, Jr.

(57) ABSTRACT

The present disclosure describes a differential-type carbon dioxide sensor, which includes a pH-electrode, a bicarbonate electrode, and a chloride electrode, and a reference electrode, which is enclosed in a chamber. The pH electrode has a pH-sensitive membrane and the bicarbonate electrode has a bicarbonate-sensitive membrane, which comprises 30% by weight of a polymer matrix, 30% by weight of a carbonate or bicarbonate ion-selective material, 30% by weight of a plasticizer, and 10% by weight of a lipophilic additive based on total weight of the bicarbonate-sensitive membrane. Further, the chloride electrode has a membrane with no selectivity towards bicarbonate and towards salicylate, which is within a predetermined therapeutic range having a concentration of salicylate less than 1.5 mmol/L. The pH electrode, the bicarbonate electrode, and the chloride electrode operate in tandem with each other.

9 Claims, 7 Drawing Sheets

(56) References Cited

U.S. PATENT DOCUMENTS

| | | |
|---|---|---|
| 5,789,255 A | 8/1998 | Yu |
| 5,876,952 A | 3/1999 | Shieh |
| 6,350,524 B1 * | 2/2002 | Lee .................... G01N 27/333 |
| | | 205/779 |
| 6,773,564 B1 | 8/2004 | Yugawa et al. |
| 7,005,048 B1 | 2/2006 | Watanabe et al. |
| 7,189,314 B1 * | 3/2007 | Pace .................. G01N 33/1886 |
| | | 204/412 |
| 2002/0028767 A1 | 3/2002 | Jensen et al. |
| 2003/0186846 A1 | 10/2003 | Hoeg-Jensen et al. |
| 2005/0145490 A1 | 7/2005 | Shinno et al. |
| 2006/0263296 A1 | 11/2006 | Kinniburgh et al. |
| 2010/0167416 A1 | 7/2010 | Kabilan et al. |
| 2013/0060105 A1 | 3/2013 | Shah et al. |
| 2013/0344619 A1 | 12/2013 | Crane et al. |
| 2016/0054257 A1 * | 2/2016 | Ishige .................. G01N 27/333 |
| | | 205/789 |

FOREIGN PATENT DOCUMENTS

| | | |
|---|---|---|
| GB | 2020424 A | 11/1979 |
| WO | 0181919 A2 | 11/2001 |

* cited by examiner

DIFFERENTIAL CARBON DIOXIDE SENSOR

TECHNICAL FIELD

This disclosure relates to differential-type carbon dioxide sensors or electrodes. More specifically, this disclosure invention relates to a three-way differential-type carbon dioxide sensor.

BACKGROUND ART

Quantification of total carbon dioxide species, i.e., carbon dioxide ($CO_2$), bicarbonate ($HCO_3$), and carbonate ($CO_3$), can be applied to various fields including those related to process analysis, environmental analysis, and in clinical analysis. For example, it can be applied for analyzing clinical samples in the medical diagnostic fields, for regulating combustion processes in chemical analysis fields, for diagnosing the severity of the greenhouse effect, and for measuring the indexes related to aquatic ecosystem in an environmental field. The exact measurement of dissolved carbon dioxide becomes increasingly significant.

In a human body, determination of the total carbon dioxide species is related to the acid-base and electrolyte balance in the human body which is regulated by pulmonary and renal mechanisms. The main ion connecting these two regulative pathways is the bicarbonate ion ($HCO_3^-$). The malfunction in either of these two mechanisms is manifested by changes in the bicarbonate concentration accompanied by changes in pH and dissolved partial pressure of carbon dioxide, or $pCO_2$. The free carbon dioxide is dissolved in blood plasma and hydrated to form carbonic acid ($H_2CO_3$), which is in turn dissociated into hydrogen ion ($H^+$) and bicarbonate ion ($HCO_3^+$). Since the total content of carbon dioxide ($CO_2$ gas, $H_2CO_3$, $HCO_3^-$, $CO_3^{2-}$) in blood plasma affects the acid-base balance and pH of blood, as well as being an index for pulmonary ventilation, alveolar gas exchange capacity, and the quantity of the gas transferred to somatic tissues from blood, it is very important to accurately measure the levels of carbon dioxide dissolved in blood. The value of total $CO_2$ in biological fluids such as human blood or serum or plasma can be calculated if pH and the concentration of one form of $CO_2$ ($pCO_2$, $HCO_3$ or $CO_3$) are measured as all are linked by Henderson Hasselbalch equation.

One way to measure concentrations of carbon dioxide is to use a Severinghaus-type carbon dioxide gas sensor, wherein an external reference electrode, a pH-sensitive working electrode and a gas-permeable membrane are simultaneously housed in one sensor body. The Severinghaus-type carbon dioxide gas sensor is immersed in internal filling solution (IFS), which is unbuffered. $CO_2$ permeates through the gas permeable membrane and dissolves in the internal filling solution, thereby changing the pH of the IFS. This change in pH is directly proportional to the $pCO_2$. The Severinghaus-type carbon dioxide gas sensor has a mechanically complicated structure and suffers interference from volatile organic acids. Another disadvantage of the Severinghaus-type carbon dioxide gas sensor is difficulty in miniaturization of the sensor, because the reference electrode is incorporated inside the sensor body. Further, the Severinghaus-type carbon dioxide gas sensor suffers from the disadvantage of being poor in detection limit.

Another way to measure concentrations of carbon dioxide is by use of a differential-type carbon dioxide gas sensor, wherein a working electrode and a reference electrode are separated in different sensor bodies. The differential-type carbon dioxide gas sensor comprises a working electrode composed of an unbuffered inner reference solution and a pH-sensitive gas-permeable membrane; and a reference electrode composed of a buffered inner reference solution and the same pH-sensitive gas-permeable membrane as that in a working electrode.

In the differential-type carbon dioxide gas sensor, charge separation and the accompanying potential difference occur at 4 different interfaces: E (ext1) between the pH-sensitive gas-permeable membrane of the working electrode and the sample solution; E (ext2) between the pH-sensitive gas-permeable membrane of the reference electrode and the sample solution; E (int1) between the pH-sensitive gas-permeable membrane of the working electrode and the unbuffered inner reference solution; and E (int2) between the pH-sensitive gas-permeable membrane of the reference electrode and the buffered inner reference solution.

When such charge separations occur, E (ext1) and E (ext2) have the same value and thus can be counterbalanced, as the same pH-sensitive gas-permeable membranes are used. On the other hand, the charge separation E (int2) between the pH-sensitive gas-permeable membrane of the reference electrode and the buffered inner reference solution is maintained at a constant value as the reference solution is buffered. Therefore, a change in carbon dioxide levels in a sample solution causes only the charge separation E (int1) between the pH-sensitive gas-permeable membrane and the unbuffered inner reference solution of the working electrode, so that the resulting potential change enables the carbon dioxide levels of the sample solution to be quantitatively detected.

A promising approach is to use a carbonate-selective electrode, which usually employ trifluoroacetophenone derivative as neutral carriers for carbonate. However so far the applications of carbonate selective electrodes have been limited by insufficient sensitivity and selectivity of the electrodes. The sensitivity problem is usually dealt with by increasing the pH of the sample, or pretreatment of sample, which is not possible on an analyzer, such as a blood gas analyzer. Traditionally, multiple formulations have been proposed to use the carbonate-selective electrode in series with other ion-selective electrodes commonly employed in automated clinical chemistry/electrolyte analyzers by reduced interference from anions such as salicylate in the measurement range of 5-50 mm total $CO_2$ at physiological pH without pretreatment of the sample. Normal salicylate level in blood are typically less than 0.1 mmol/L, but therapeutic levels for aspirin users are approximately 1.5 mmol/L. Formulations with higher selectivity towards Salicylate could cause substantial positive errors in total $CO_2$ measurements. One of the existing approach describes a buffer overcoat layer which is supposed to eliminate organic anion interferences.

Therefore, there exists a need for a robust arrangement of differential carbon dioxide gas sensors and related systems and methods that prevent elevated $CO_2$ signal within therapeutic levels of salicylate in biological fluids.

SUMMARY OF INVENTION

This disclosure describes systems and methods for implementing a three-way differential-type carbon dioxide sensor.

The subject matter of this application may involve, in some cases, interrelated products, alternative solutions to a particular problem, and/or a plurality of different uses of a single system or article.

Embodiments of the present disclosure include a differential-type carbon dioxide sensor comprising a pH-electrode, a bicarbonate electrode, and a chloride electrode, and a reference electrode, which is enclosed in a chamber. The pH electrode has a pH-sensitive membrane, the bicarbonate electrode has a bicarbonate-sensitive membrane, and the chloride electrode has a chloride-sensitive membrane with no selectivity towards bicarbonate and selectivity towards salicylate, which is within a predetermined therapeutic range. The pH electrode, the bicarbonate electrode, and the chloride electrode operate in tandem with each other.

Other and further aspects and features of the disclosure will be evident from reading the following detailed description of the embodiments, which are intended to illustrate, not limit, the present disclosure.

BRIEF DESCRIPTION OF DRAWINGS

To further aid in understanding the disclosure, the attached drawings help illustrate specific features of the disclosure and the following is a brief description of the attached drawings.

DISCLOSURE OF EMBODIMENTS

The detailed description set forth below in connection with the appended drawings is intended as a description of presently preferred embodiments of the invention and does not represent the only forms in which the present invention may be constructed and/or utilized. The description sets forth the functions and the sequence of steps for constructing and operating the invention in connection with the illustrated embodiments.

In referring to the description, specific details are set forth in order to provide a thorough understanding of the examples disclosed. In other instances, well-known methods, procedures, components, and materials have not been described in detail as not to unnecessarily lengthen the present disclosure.

It should be understood that if an element or part is referred herein as being "on", "against", "in communication with", "connected to", "attached to", or "coupled to" another element or part, then it can be directly on, against, in communication with, connected, attached or coupled to the other element or part, or intervening elements or parts may be present. When used, the term "and/or", includes any and all combinations of one or more of the associated listed items, if so provided.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated.

Various operations may be described as multiple discrete operations in turn, in a manner that may be helpful in understanding embodiments; however, the order of description should not be construed to imply that these operations are order dependent.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

In the following description, reference is made to the accompanying drawings which are illustrations of embodiments in which the disclosed invention may be practiced. It is to be understood, however, that those skilled in the art may develop other structural and functional modifications without departing from the novelty and scope of the instant disclosure.

This disclosure describes systems and methods for implementing three-way differential-type carbon dioxide sensors.

The present disclosure relates to a macro, long-lasting, maintenance-free differential-type (3-way) electrode or sensor being able to quickly measure levels of bicarbonate/carbon dioxide (response time less than 5 seconds) dissolved in whole blood, plasma, serum or liquid solution. The electrode works in conjunction with pH electrode with buffered IFS (internal filling solution), bicarbonate electrode (with buffered IFS) having high selectivity towards interfering ion Chloride (10 to 1). More importantly, the present disclosure relates to the ability of measuring bicarbonate and $pCO_2$ (partial pressure of carbon dioxide) by purposefully decreasing the selectivity of $HCO_3$ over Chloride, so that the $HCO_3$ electrode could be calibrated with interfering Chloride ion.

Another aspect of the present disclosure includes to report the pH, $pCO_2$ data at 37 degree Celsius by finding the temperature coefficient for the pH and $pCO_2$ measurement. By using macro electrodes, which operate at room temperatures and housing the electrodes in a big reference electrode, which has relatively large pool of reference filling solution compared to other electrodes equilibrated at room temperature, electrodes don't have to be heated to 37° C. or maintained at 37° C. to report the results at 37° C. By placing a temperature transducer within the reference fill solution, the operating room temperature, which is used to correct for the pH and pCO2 value at 37° C. By not heating the electrode, the electrodes last longer due to reduced loss of IFS and also reduced leaching of the ionophore. This paves the path to manufacture blood gas analyzer without pre-heater circuit to maintain electrodes at 37° C.

This disclosure describes numerous specific details in order to provide a thorough understanding of the present invention. One skilled in the art will appreciate that one may practice the present invention without these specific details. Additionally, this disclosure does not describe some well-known items in detail in order not to obscure the present invention.

Figure 1:
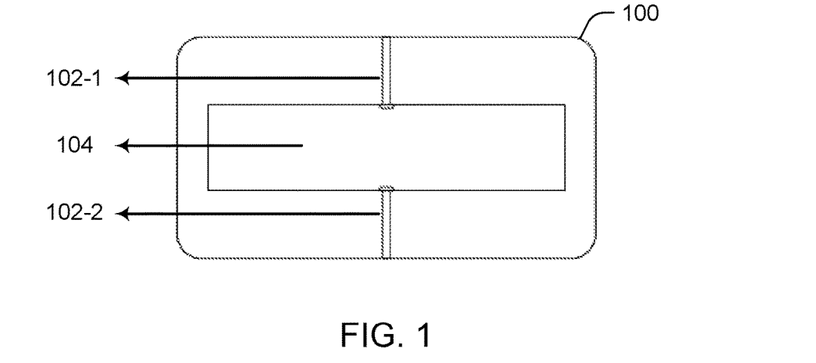
FIG. 1 is a schematic view of a base body for an ion-selective electrode.

FIG. 1 is a schematic view of a base body for an ion-selective electrode. The ion-selective electrode (ISE), also termed as membrane electrode, may be defined as an electrode having a membrane that selectively responds to ions present in an analyte sample and converts an ion activity into an electrical potential across the membrane. ISE may be made up of a variety of components that may be assembled together using a variety of techniques known in the art, related art, or developed later including casting.

These components may include a base body 100 that may provide a platform for constructing a customized electrode having a predetermined type of membrane based on an intended application. The base body 100 may be made up of any suitable solid material known in the art, related art, or developed later that is stiff, non-porous, non-conductive, chemically inert, thermally stable, and corrosion resistant under predetermined ranges of temperature, pressure, and moisture. In one embodiment, the base body 100 may be made of polyvinyl chloride (PVC) having high molecular weight; however other suitable materials including glass, PolyCarbonate, acrylic in combination or alone, can be contemplated and employed.

The base body 100 may include a cavity 104 formed therein using any of the manufacturing processes known in the art, related art, or developed later. In one embodiment, the cavity 104 may be created based on a solid material, such as those discussed above, being formed as a support matrix around a mold (not shown), which may be then removed to form the cavity 104. For example, the solid material may be sealed within a rectangular mold with an inner portion having dimensions and design equivalent to a predetermined cavity volume. The solid material may in a heated or molten state for being introduced into the mold and allowed to cool down. Upon being cooled, the solid material may be gently removed sufficient to expose an inner portion of the mold. Such inner exposed portion of the mold may correspond to the predetermined cavity opening dimension. The exposed portion of the mold can then be removed to leave an open cavity volume surrounded by the solid material with one or more openings in the surrounding walls. The cooled solid material having the cavity 104 and the openings may form the base body 100 for the ISE. In some embodiments, the mold may be synthesized by using zinc stearate as a stabilizer and assists in easy release of the base body 100 from the mold; however, other suitable releasing agents known in the art, related art, or developed later including Tin stearate may be used.

The cavity 104 may have any suitable cross-section that supports easy positioning of other components such as separation discs and membrane. For example, the cavity 104 may have a rectangular cross-section; however, other suitable cross-sections including elliptical, oval, polygon, irregular, etc. may be contemplated. The predetermined cavity volume may be sufficient to substantially receive these components. In some embodiments, the base body 100 may have inner surface of the base body walls, which enclose the cavity 104, being coated with any of a variety of anti-friction materials known in the art, related art, or developed later including Polytetrafluoroethylene (PTFE).

Further, the base body 100 may include the one or more openings in communication with the cavity 104. These openings may be located on a front surface and a back surface of the base body 100 and provide easy access to the cavity 104 for placement of the other components of the ISE. At least one of the openings on each of the front surface and the back surface may be aligned to each other along a common central axis passing through the openings. Furthermore, across an axis extending parallel to the base body 100 and through the center of the cavity 104, the base body 100 may be divided into an upper portion and a lower portion, where the upper portion includes a first lumen 102-1 having a first end that opens on the top surface and a second end that opens in the cavity 104 within the base body 100. Similarly, the lower portion may include a second lumen 102-2 having a first end that opens on the bottom surface and a second end that opens in the cavity 104 of the base body 100.

Each of the first lumen 102-1 and the second lumen 102-2 (collectively, lumens 102) may be formed using any of a variety of techniques known in the art, related art, or developed later. For example, the lumens 102 may be formed by focused drilling through the upper portion and the lower portion of the base body 100. In some embodiments, the lumens 102 may be coated with any of a variety of anti-friction materials, such as those mentioned above, which may reduce friction between the lumens 102 and a fluid (e.g., analyte sample) or any device engaging with the lumens 102. In one embodiment, the first lumen 102-1 may be longitudinally aligned to the second lumen 102-2. Other suitable arrangements involving oppositely aligned one or more lumens may be contemplated by a person having ordinary skill in the art. The lumens 102 may have inner diameters having dimensions that allow unrestricted flow of a predetermined fluid, e.g., the analyte sample, through the base body 100 via the cavity 104. In one aspect, the lumens 102 may have similar dimensions; however, in some embodiments, the first lumen 102-1 and the second lumen 102-2 may have relatively different dimensions to facilitate an intended sample fluid flow.

Figure 2:
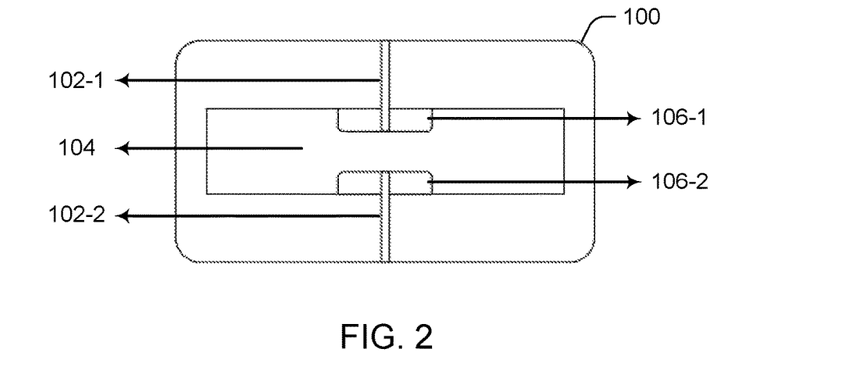
FIG. 2 is a schematic view of the ISE base body 100 with separator discs.

FIG. 2 is a schematic view of the ISE base body 100 with separator discs. The base body 100 may be introduced with one or more separator discs within the cavity 104 such that the separator discs provide a separation between the base body 100 and a membrane. The separator discs may be made up of any high purity material known in the art, related art, or developed later that may be rigid, flexible, or semi-rigid. Exemplary materials may include metals, polymers, composites, alloys, or the like. For example, the separator discs may be made of high purity PVC; however, other suitable materials can be contemplated. In one embodiment, a first high purity PVC disc 106-1 may be attached in contact with the upper portion from within the cavity 104 of the base body 100. Similarly, a second high purity PVC disc 106-2 may be attached to the lower portion from within the cavity 104 of the base body 100. Such attachment may be performed using any of a variety of methods known in the art, related art, or developed later. In one example, the high purity PVC discs 106-1 and 106-2 (collectively, PVC discs 106) may be welded with tetrahydrofuran (THF) to the base body 100 within the cavity 104.

Further, the first high purity PVC disc 106-1 and the second high purity PVC disc 106-2 (collectively, PVC discs 106) may include a first hole and a second hole respectively, such that the first hole aligns with the first lumen 102-1 and the second hole aligns with the second lumen 102-2 based upon the PVC discs 106 being placed within the cavity 104. The PVC discs 106 may be separated by a predetermined spacing for receiving a predetermined membrane. Dimensions of the PVC discs 106 may be suitably selected based on dimensions of the membrane. Such arrangement of the PVC discs 106 within the cavity 104 allows to avoid the membrane from being in contact with the base body 100 and prevents contamination of the membrane with impurities in the base body 100, thereby enhancing membrane life.

Figure 3:
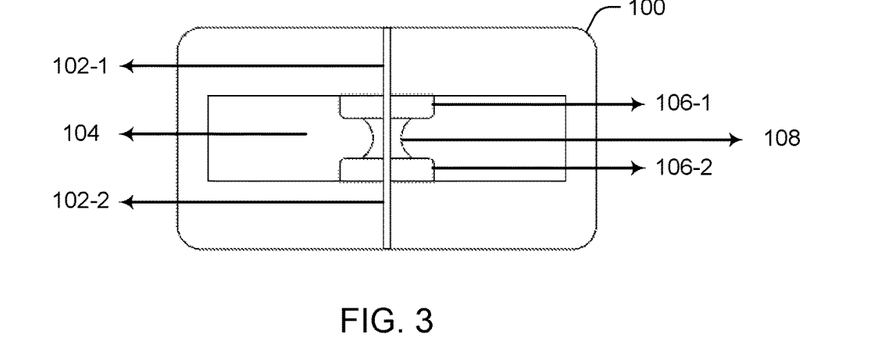
FIG. 3 is a schematic view illustrating a membrane in the base body.

FIG. 3 is a schematic view illustrating a membrane in the base body 100. A predetermined membrane 108 may be secured between the separator discs, e.g., PVC discs 106, using a variety of techniques known in the art, related art, or developed later including, but not limited to, snap fit, screw fit, luer-lock, and gluing that may be chosen based on the material of the separator discs and the membrane 108. For example, the membrane 108 may be secured between the PVC discs 106 by the membrane 108 being welded (or being fused) with THF to the separator discs within the cavity 104. In one embodiment, the membrane 108 may be a bicarbonate sensitive membrane made up of any of a variety of suitable materials known in the art, related art, or developed later. For example, the membrane 108 may be a signal generating membrane with active ingredients, e.g., a polymer matrix, ionophore, ionic additives, and plasticizers mixed in predetermined quantities based on intended properties and applications of the membrane 108.

As a polymer matrix, any suitable material with good adhesiveness, biocompatibility with bodily fluids (e.g., blood, saliva, etc.), chemically inert nature, predetermined electrochemical properties, and high molecular weight may be used, either alone or in combination. Such exemplary materials include, but not limited to, PVC, polyurethane (PU), and silicone rubber.

The ionophore may be selectively chosen based on the intended affinity of the gas-sensitive membrane 108 towards a specific type of ions. In one embodiment, P-Decyl-α, α, α-trifluoroacetophenone may be used as a carbonate neutral carrier-based ionophore in order to prepare a carbonate/bicarbonate ion-selective membrane 108. However, other suitable materials known in the art, related art, or developed later may be used.

The plasticizer used may include, but not limited to, DOS (bis(2-ethylhexyl)sebacate), NPOE (2-nitrophenyl octyl ether), or any other suitable material known in the art, related art, or developed later, either alone or in combination.

The lipophilic additive used may be a variety of materials known in the art, related, or developed later including, but not limited to, Tridodecylmethylammonium Chloride (TDMAC).

Preparation Example: Preparation of pH-Sensitive Membrane

In a predetermined amount of tetrahydrofuran, high molecular weight PVC may be dissolved as a polymer matrix at an amount of 29.8% by weight based on the total weight of the membrane 108, TDDA (tridodecyl amine) in the range of 9.3% by weight as a hydrogen-selective material, DOS (bis(2-ethylhexyl sebacate) in the range of 59.6% by weight as a plasticizer, and KTpClPB (potassium tetrakis [4-chlorophenyl]borate) in the range of 1.3% by weight as a lipophilic additive, after which the resulting solution may be dried at room temperature for a predetermined time, e.g., 1-2 days, to prepare a pH-sensitive membrane.

Preparation Example: Preparation of Bicarbonate-Sensitive Membrane

In a predetermined amount of tetrahydrofuran, high molecular weight PVC may be dissolved as a polymer matrix at an amount of 30% by weight based on the total weight of the membrane 108, P-Decyl-α, α, α-trifluoroacetophenone in the range of 30% by weight as a bicarbonate-selective material, DOS (bis(2-ethylhexyl sebacate) in the range of 30% by weight as a plasticizer, and TDMAC in the range of 10% by weight as a lipophilic additive and to enhance chloride sensitivity, after which the resulting solution may be dried at room temperature for a predetermined time, e.g., 1-2 days, to prepare a bicarbonate-sensitive membrane.

Preparation Example: Preparation of Chloride-Sensitive Membrane

In a predetermined amount of tetrahydrofuran, high molecular weight PVC may be dissolved as a polymer matrix at an amount of 35% by weight based on the total weight of the membrane 108 and TDMAC with 65% by weight as a lipophilic additive, after which the resulting solution may be dried at room temperature for a predetermined time, e.g., 1-2 days, to prepare a chloride-sensitive membrane with no selectivity towards bicarbonate and towards salicylate in the therapeutic range (salicylate less than 1.5 mmol/L).

Different types of membranes, such as those discussed above, may be created and secured between the separator discs. In one example, the membrane 108 may be tubular in shape; however, other suitable shapes including but not limited to oval, elliptical, polygon, irregular, etc. may be contemplated based on the predetermined spacing between the separator discs.

Figure 4:
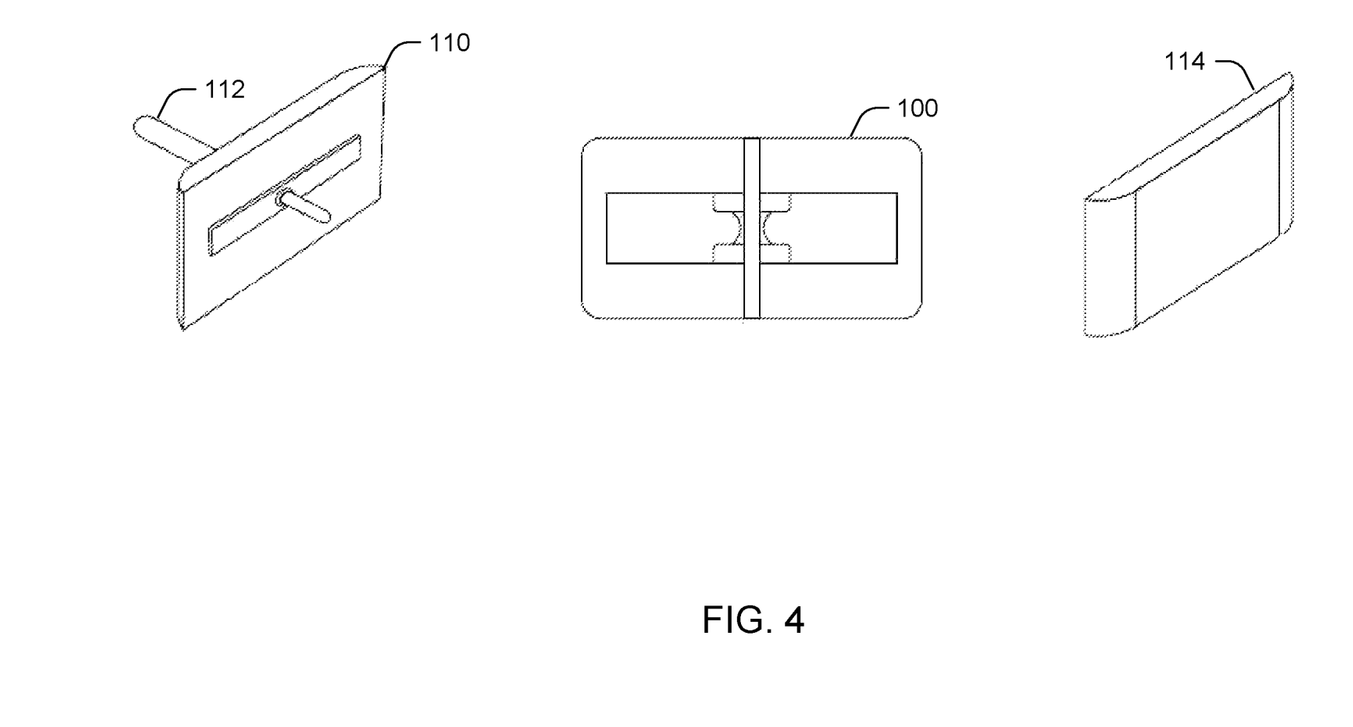
FIG. 4 is a schematic view of external components of an ISE.

FIG. 4 is a schematic view of external components of an ISE. The external components may include a back cover 110 and a front cover 114, each being made up of PVC; however, other suitable materials may be contemplated. In some embodiments, the back cover 110 and the front cover 114 may be made up of same or different materials. The back cover 110 may be attached to the back surface of the base body 100 and the front cover 114 may be attached to the front surface of the base body 100. For such attachment, the back cover 110 and the front cover 114 may be fused to the respective surfaces of the base body 100 with the help of THF solvent; however other suitable attachment techniques known in the art, related art, or developed later including, but not limited to, welding, snap fit, screw fit and gluing may be contemplated. In one embodiment, the back cover 110 may be introduced with a silver (Ag)/silver chloride (AgCl) reference pin 112 that may be inserted through an outer side of the back cover 110 and extended out from an opposing inner side of the back cover 110. The outer side may be in communication with ambient surrounding and the opposing inner side may be in communication with the cavity 104 of the base body 100.

Figure 5:
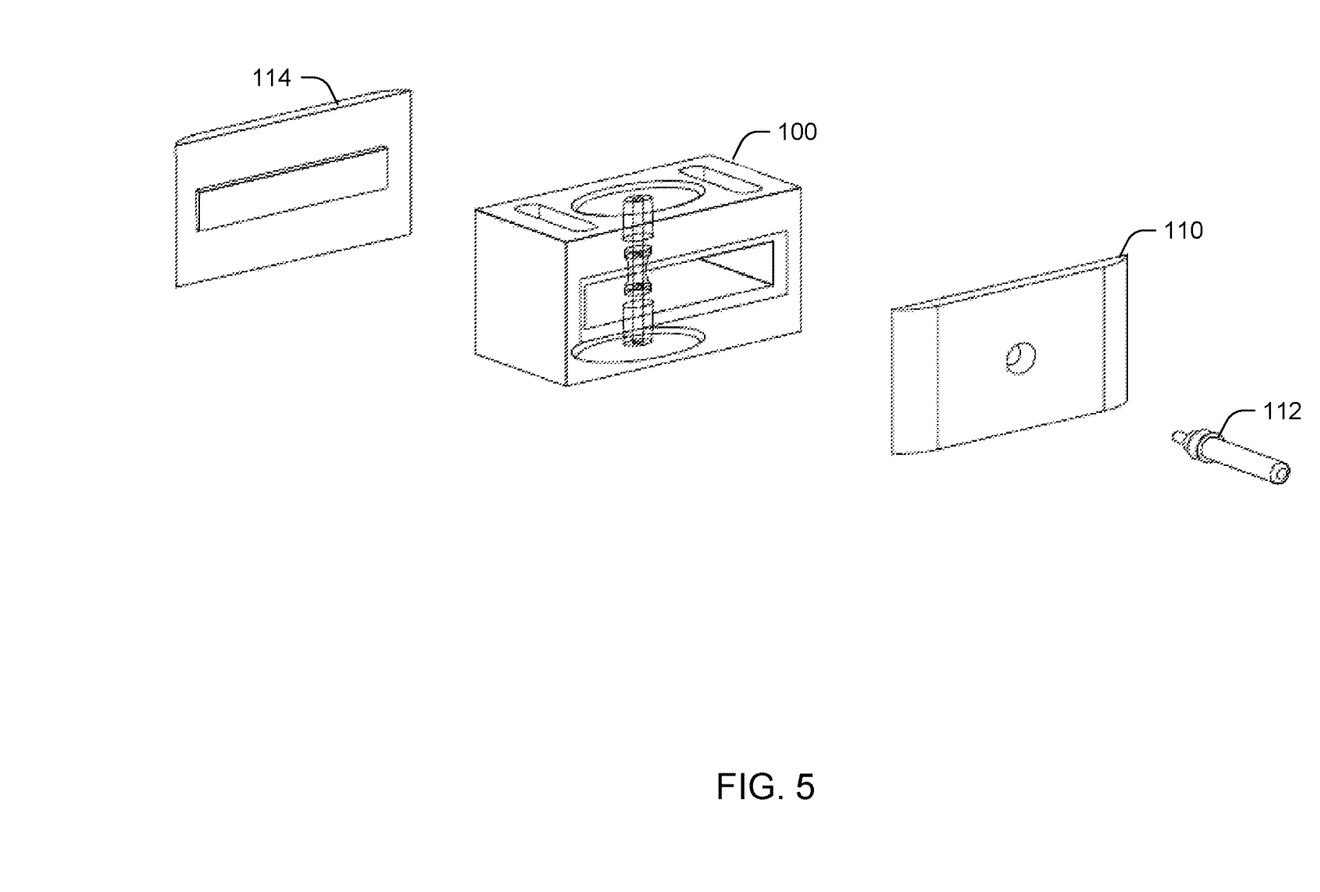
FIG. 5 shows an assembly arrangement to assemble external components with the base body.

FIG. 5 shows an assembly arrangement to assemble external components with the base body 100. In one embodiment, the external components, e.g., the back cover 110 (inserted with the Ag/AgCl pin 112) and the front cover 114 can be assembled and secured to the base body 100 using any of the techniques known in the art, related art, or developed later. For example, the inner side of the back cover 110 may include a raised plate that may friction fit into the opening on the back surface of the base body 100. Similarly, an inner side of the front cover 114 may include similar raised plate that may friction fit into the opening on the front surface of the base body 100. However, a person having ordinary skill in the art can contemplate other suitable techniques including, but not limited to, plastic welding and gluing for securing the back cover 110 and the front cover 114 to the base body 100.

These external components upon being assembled with the base body 100 (including the separator discs, e.g., PVC discs, and the membrane, e.g., PVC membrane) may form an assembled electrode. In one embodiment, the external components may be assembled with the base body 100 having a bicarbonate-sensitive membrane, such as the one discussed above, to form a bicarbonate ($HCO_3$) electrode. The assembled $HCO_3$ electrode with the $HCO_3$-sensitive membrane may be used as a sensor for sensing bicarbonate ions and a partial pressure of carbon dioxide in an analyte sample passing through it. Such $HCO_3$ electrode may be also referred to as bicarbonate sensor.

In some embodiments, the base body 100 may include one or more recesses on a top surface and around the first lumen 102-1 of the base body 100. These recesses may be configured to receive projections of relatively similar dimensions on a bottom surface of another base body or electrode so as to stack that another base body on top of the base body 100 by a male/female engagement.

Figure 6:
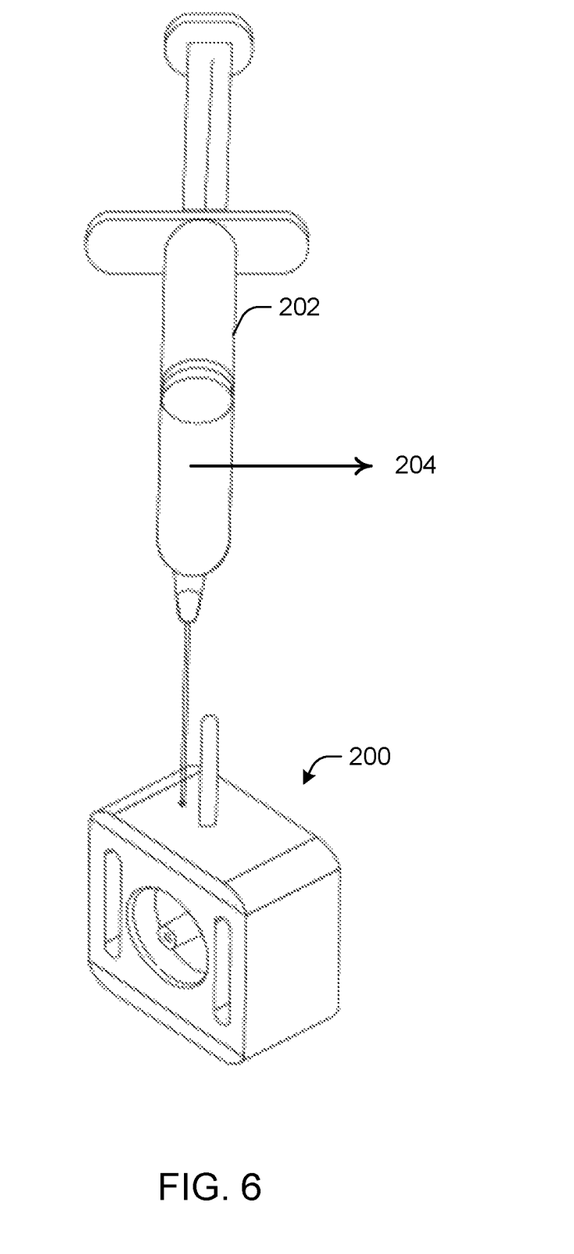
FIG. 6 is schematic of injecting a strongly buffered internal filling solution (IFS) into an assembled electrode.
Figure 7:
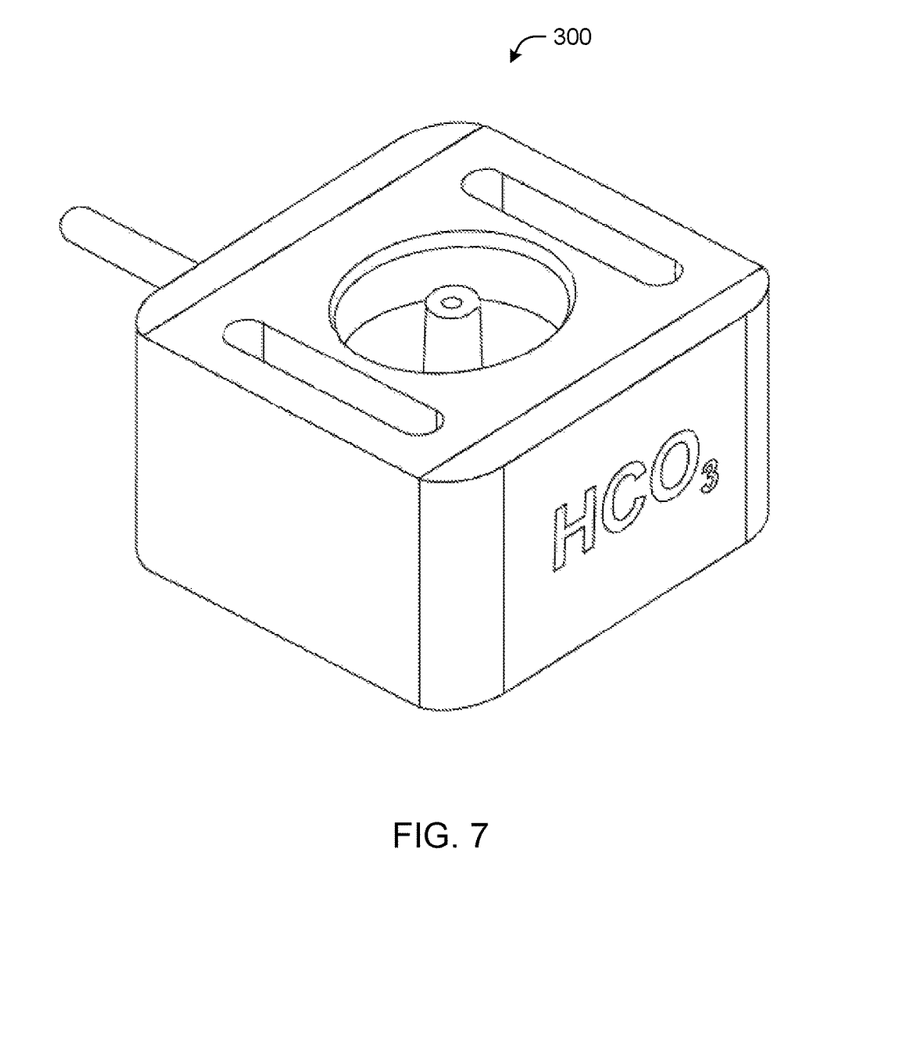
FIG. 7 is schematic of a completely assembled electrode.

FIG. 6 is schematic of injecting a strongly buffered internal filling solution (IFS) into an assembled electrode 200. In one embodiment, the assembled electrode may be drilled to form a passage that extends through the back cover 110 and opens into the cavity 104 using any of the techniques known in the art, related art, or developed later including electron beam drilling. The passage may have dimensions, e.g., 0.8 mm wide, relatively less than that of any of the lumens 102. The passage may be used to inject a predetermined amount, e.g., 2 mL, of the IFS 204 using any suitable mechanism, e.g., a syringe 202, to fill the cavity 104 of the assembled electrode 200. The IFS 204 may be a strong buffer solution, which may be defined as an aqueous solution having a mixture of a weak acid and its conjugate base, or vice versa, that resists changes in its pH value when small quantities of an acid or an alkali are added to it. Once the IFS 204 is injected, a passage opening on an outer surface of the back cover 110, or the whole passage, may be sealed using any suitable sealant known in the art, related art, or developed later, e.g., 12-hours epoxy. During such 12-hours epoxy curing process, the membrane 108, e.g., the $HCO_3$-sensitive membrane, may be wet and equilibrated with the IFS 204 and may not need any additional time on an assembly machine to provide a stable baseline, i.e., a baseline pH value. One such assembled $HCO_3$ electrode 300 filled with the strong buffer solution is illustrated in FIG. 7.

Figure 8:
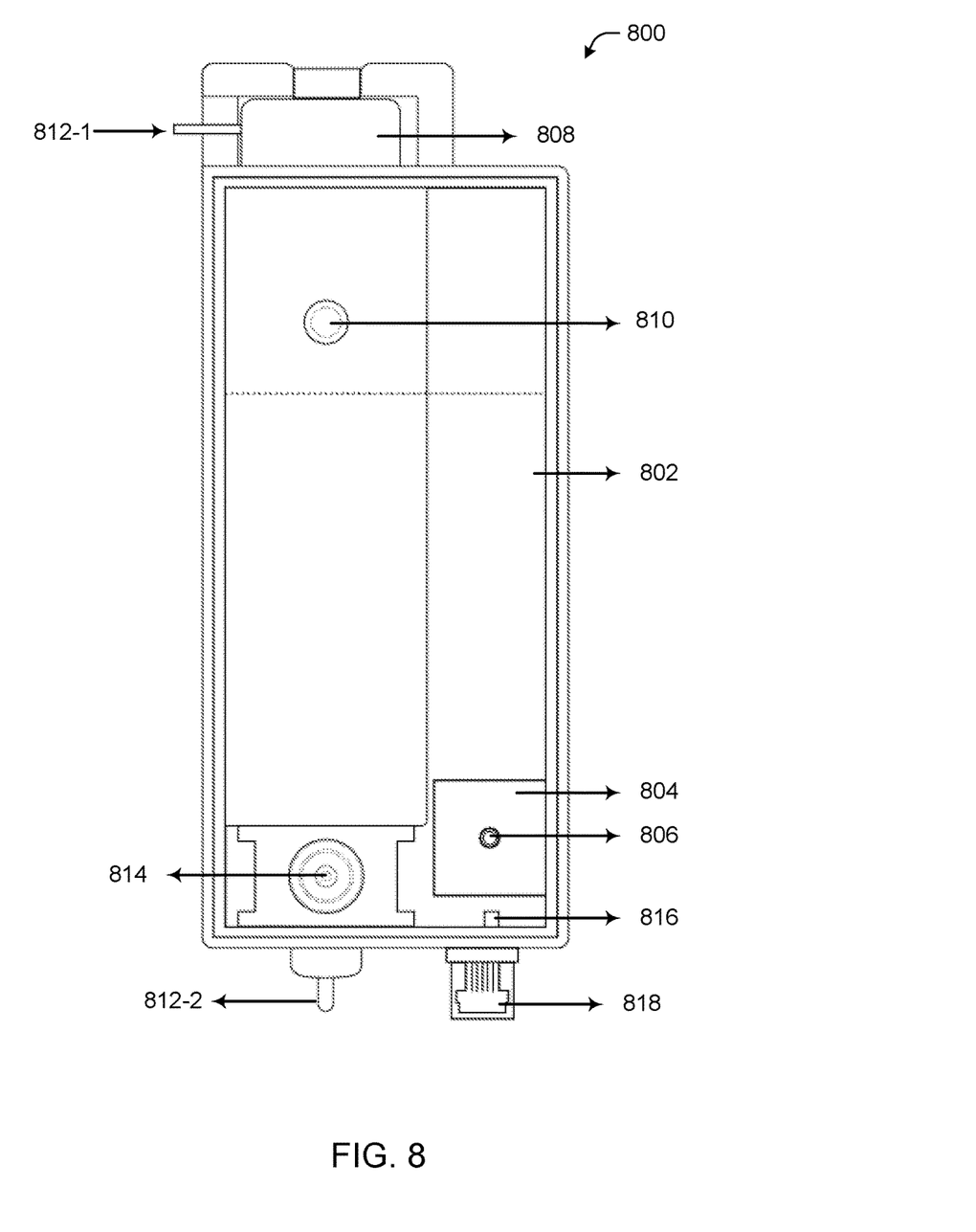
FIG. 8 is schematic of a first side of an exemplary dialysis membrane-based non-flowing double junction reference housing.

FIG. 8 is schematic of a first side of an exemplary dialysis membrane-based non-flowing double junction reference housing 800, hereinafter referred to as reference housing 800. The reference housing 800 operates as a reference electrode that includes a reference electrode chamber 804 having a double junction reference electrode (not shown) and a ceramic plug 806, which provides an interface for the reference electrode chamber 804. The reference electrode chamber 804 may be submerged under an internal filling solution (IFS) 802 filled in the reference housing 800 in a predetermined quantity, e.g., 60 ml and having a predetermined concentration, e.g., 2 mol/L KCl.

The housing 800 also includes a dialysis membrane 814 that communicates with at least one of the lumens, e.g., lumens 102, of the electrodes, e.g., the $HCO_3$ electrode 300. The dialysis membrane 814 supports outflow of the samples or calibration solutions from the reference housing 800. One end of the dialysis membrane 814 may communicate with a sample input interface 812-1 (or sample in interface 812-1) for introducing the samples or the calibration solutions into the housing 800 and another end may communicate with a sample output interface 812-2 or sample out interface 812-2 for removing the introduced samples or calibration solutions from the reference housing 800.

Further, the housing 800 includes a bubble detector 808 configured to detect an air bubble in a sample introduced through the sample in interface 812-1 and to vent out the bubble through a vent hole 810 in the reference housing 800 using any suitable arrangement known in the art, related art, or developed later. In addition, the housing 800 may include a temperature transducer 816 that may be inserted into the IFS 802 to capture the temperature of an electrode train, which may be very close to the temperature of the internal filling solution, which acts as a temperature bath. The temperature transducer 816 may be connected to a computing device with an RJ-11 connector 818; however, other suitable interface or transmission media may be contemplated. The computing device may include a desktop personal computer (PC), a personal digital assistant, a server, a mainframe computer, a mobile computing device (e.g., mobile phone, laptop, etc.), an internet appliance, and so on preconfigured or dynamically configured to analyze predetermined one or more parameters related to the sample (introduced within the reference housing 800 for being examined) or ambient temperature, pressure, or moisture conditions within the reference housing 800, to exchange or display corresponding analyzed data (with or without graphical visualizations) either independently or in combination/communication with another computing device, input device (e.g., scanner, keyboard, sensor, etc.), output device (e.g., monitor, projector screen, display screen, etc.) or a combination thereof.

Figure 9:
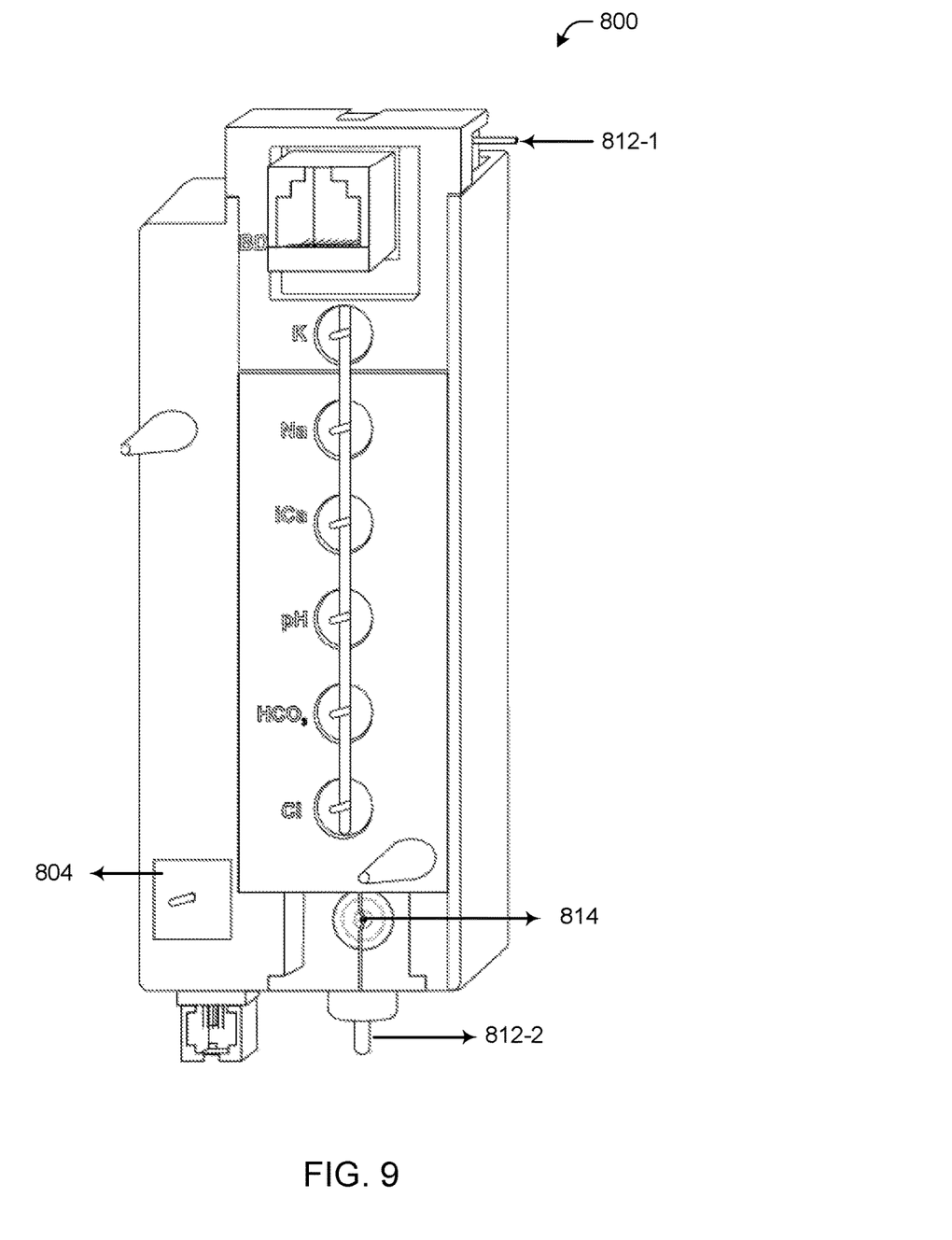
FIG. 9 is schematic of an exemplary assembled electrode train with the dialysis membrane-based non-flowing double junction reference housing of FIG. 8.

FIG. 9 is schematic of an exemplary assembled electrode train with the dialysis membrane-based non-flowing double junction reference housing 800 of FIG. 8. The electrode train includes multiple electrodes or sensors, each having a predetermined membrane being sensitive to a specific type of ions. For example, the electrodes may include membranes sensitive to ions of sodium (Na), potassium (K), ionized calcium (iCa), pH buffer solution (pH), bicarbonate ($HCO_3$) and chloride (Cl), where the corresponding electrodes may be termed as sodium electrode (Na-electrode), potassium electrode (K-electrode), calcium electrode (iCa-electrode), pH electrode, bicarbonate electrode ($HCO_3$-electrode) and chloride electrode (Cl-electrode) respectively. Each of these electrodes may be stacked over each other in a predetermined order, e.g., starting at Cl-electrode, $HCO_3$ electrode, pH electrode, iCa-electrode, Na-electrode, and K-electrode, where Cl-electrode is located at the bottom of the electrode train and adjacent to the sample out interface 812-2. The electrodes may be stacked with interfacing silicone seals to make the electrode train air tight for accomplishing a leak-proof arrangement. Further, the respective lumens, such as the lumens 102, of the stacked electrodes are longitudinally aligned with each other and the dialysis membrane 814 of the reference housing 800. Each of such electrodes may be formed with respective membranes as discussed above in the description of FIGS. 1-7.

The electrodes may be calibrated using a computing device, e.g., once in every 4 or 8 hours, or as suitable based on the intended effect to be achieved. For example, when calibrating the $HCO_3$ electrode, typically, bicarbonate based standard IFS in the $HCO_3$ electrode vary in composition due to loss of $CO_2$ from the electrodes, and in turn change the pH of a communicating standard solution within the electrode. The loss of the $CO_2$ can be reduced by maintaining pH of the standard IFS above 7.5. Further, conventionally, the pH electrode needs two calibrating standards, namely Cal A based on a pH buffer maintained at 7.38 with known amount of Na, K, iCa, Li and Cl, and Cal B based on a pH buffer maintained at 6.84 with known amount of Na, K, iCa, Li and Cl. These two standards are used to calibrate all the electrodes (Na, K, iCa, Li, pH, HCO$_3$ and Cl). In one embodiment, since the HCO$_3$ electrode has 10 to 1 selectivity towards Chloride, each electrode is calibrated with the help of known Chloride concentrations is Cal A and Cal B. Conventionally most of the blood gas analyzers, use additional two calibration standards (Cal C and Cal D). Each of these calibration standards, i.e., Cal A, Cal B, Cal C, and Cal D, were implemented with same electrolyte composition (Na, K, iCa, Li, pH and Cl), but different concentrations of HCO$_3$ to generate a desired value of pCO$_2$. The pH of each solution may be measured prior to determining the pCO$_2$ concentrations based on the known bicarbonate concentration. At pH 7.6, approximately 3.33% of the HCO$_3$ stays in CO$_2$ form and 96.7% stays in HCO$_3$ form. Thus it is safer to calibrate using bicarbonate based solution as analyte.

In one embodiment, the formulation of the bicarbonate electrode has been purposely modified to ensure it retains enough selectivity towards Chloride, which is a more stable anion in standard solutions. Such formulation provides selectivity of 10 to 1 selectivity towards bicarbonate to chloride. The bicarbonate electrode is calibrated using Cal A which contains a predetermined concentration of Chloride, e.g., 125 mM (equivalent to 12.5 mM HCO$_3$) and Cal B which contains a predetermined concentration of Chloride, e.g., 45 mM (equivalent to 4.5 mM HCO$_3$). In addition to Cal A and Cal B, Cal C may be measured to calculate the selectivity of the HCO$_3$ electrode towards the bicarbonate over Chloride. This selectivity coefficient may be used to calculate a slope factor. Cal C may be formulated to ensure that the pH of the Cal C is approximately at 7.6 to reduce loss of CO$_2$ by outgassing. In addition to that, Cal C may have a predetermined concentrations of HCO$_3$ (e.g., 35 mM) and Chloride (e.g., 125 mM), which is same as Cal A, thereby reducing the need for Cal D. During the sample analysis, the measurements mV of the sample solution may be compared to Cal A, which has stable chloride anion being used as interfering anion, to calibrate the bicarbonate electrode and also use chloride anion in Cal A for one-point calibration during the sample analysis. Therefore, the use of calibration standard may be reduced to just one to determine the selectivity of HCO$_3$ over Chloride by using the formulation of Cal C and Cal A exactly same, except Cal C pack may have a predetermined concentration of 35 mM HCO$_3$ with same Chloride concentration of 125 mmol/L. Comparison of signals from Cal A and Cal C may provide the selectivity coefficient or slope factor for the bicarbonate electrode. Such use of three calibration standards in place of four, is unique as the bicarbonate electrode is calibrated with an interfering ion.

Further, for each of the electrodes, the electrical potential on both sides of a respective membrane at the membrane-solution junction may not be stable. In fact, the measured voltage may not be expected zero when no target ion is present and may not be necessarily always positive when the target ion is present as it all depends on the difference between a particular ISE voltage and the sum of all the other voltages in the circuit. However, the magnitude of this potential may be the same for all measurements of standards and samples and may be thus eliminated during the calibration process.

In one embodiment, a combination of the pH-electrode, the HCO$_3$-electrode, and the Cl-electrode operate in tandem with each other as a three-way differential carbon dioxide sensor (hereinafter referred to as 3-way CO$_2$ sensor), which may provide the bicarbonate (HCO$_3$) and CO$_2$ measurements. However, the pH electrode may be a standalone electrode and may not be part of a differential setup. The signal generated or measurements performed by the pH electrode, i.e., by a pH-sensitive membrane of the pH electrode, may be independent of the measurements performed by the bicarbonate (HCO$_3$) or the chloride (Cl) electrodes. The pH of a sample measured by the pH electrode may be used to calculate the pCO$_2$ by the following exemplary algorithm of Equation 1:

$$pCO_2 = HCO_3 \times 10^{(7.604-pH)} \text{ mmHg} \tag{1}$$

The pH-electrode may include a pH-sensitive membrane and filled with a predetermined quantity of strongly buffered internal filling solution, e.g., made up of 99.0 mM MOPSO acid, 1.0 mM sodium MOPSO, 100 mM NaCl and preservatives maintained at pH 4.75. However, other suitable strongly buffered solutions known in the art, related art, or developed later may be contemplated. In some embodiments, the pH electrode may be a macro electrode, with 2 ml of the internal filling solution, which may provide the pH electrode long life time (above 1 year) and make it maintenance-free.

The HCO$_3$ electrode (with a membrane formulated by using the HCO$_3$-sensitive membrane and including a strongly buffered IFS as discussed above) may be constructed to allow unrestricted flow a sample, or calibration solutions, through the strongly buffered IFS including, but not limited to, e.g., a solution made of 99.0 mM MOPSO acid, 1.0 mM sodium MOPSO, 100 mM NaCl.

The TDMAC based chloride electrode (or Cl-electrode) may have no selectivity towards bicarbonate and towards salicylate being within a predetermined therapeutic range (e.g., salicylate less than 1.5 mmol/L) in the sample solution. The Cl-electrode may use no plasticizer and may be constructed similar to the pH-electrode, but with an unbuffered internal filling solution (e.g., 100 mM NaCl).

Electrochemical Circuit for an Ion-Selective Electrode Based Measurement of Carbon Dioxide The electrode train behaving as a working electrode (which has the pH-electrode as its own internal reference electrode) and the double junction reference electrode behaving as an external reference electrode are immersed in the IFS within the reference housing 800. The electrochemical circuit may be completed by connecting the electrode train as anode and the external reference electrode as cathode to a sensitive milli-volt (mV) meter using low-noise cables and connectors. In one embodiment, an anode side of the voltmeter may be parallel connected to each of the electrodes in the electrode train. A potential difference may be measured across an ISE membrane, e.g., the HCO$_3$-sensitive membrane, when the target ions (i.e., bicarbonate ions) interact with the membrane.

Operation

At equilibrium, a potential at each of the membranes (i.e., pH-sensitive, HCO$_3$-sensitive, and Cl-sensitive membranes) of the 3-way CO$_2$ sensor may be dependent on the concentration of the target ions outside the respective membranes.

A sample (e.g., blood, saliva, serum, etc.), in which pCO$_2$ is to be measured, may be introduced into the reference housing 800 from the sample in interface 812-1. Upon such introduction, the sample may flow through the electrode train including the 3-way CO$_2$ sensor. In the pH-electrode, the sample may flow through the pH ionophore constructed with the strongly buffered internal filling solution, therefore diffused carbon dioxide may not change the pH in the strongly buffered IFS contained in the pH-electrode. Further as the sample flows through the $HCO_3$ electrode with its strongly buffered internal filling solution, the diffused carbon dioxide may not change the pH in this, which in turn may not change the anionic composition of the internal filling solution as no $HCO_3$ may be formed as the pH of the $HCO_3$-electrode's IFS may be maintained close to 4.75 ph. As the sample further flows through the Cl-electrode but with an unbuffered internal filling solution, the diffusion of the carbon dioxide may have no apparent effect on the pH-baseline of the Cl electrode because the Cl-electrode membrane has no selectivity towards bicarbonate, pH change, bicarbonate formation in this unbuffered internal filling solution or presence of salicylate within a therapeutic concentration of less than 1.5 mmol/L. Due to change in concentration of $HCO_3$ and Cl ions across the 3-way $CO_2$ sensor and the external reference electrode, the corresponding generated potential difference may be measured by the voltmeter for measuring the total content of carbon dioxide ($CO_2$ gas, $H_2CO_3$, $HCO_3^-$, $CO_3^{2-}$) in the sample.

Further since pH and $pCO_2$ measurements are temperature dependent, the reference housing 800 may further include a built-in digital thermometer (e.g., DS18S20) immersed in the 60 mL internal filing solution, such that the thermometer provides 9-bit Celsius temperature measurements. In one embodiment, the DS18S20 thermometer may communicate over a 1-Wire bus, which may require only one data line (and ground) for communication with a central microprocessor of the connected computing device. The DS18S20 thermometer may have an operating temperature range of −55° C. to +125° C. and may be accurate to ±0.5° C. over the range of −10° C. to +85° C. In addition, the DS18S20 may derive power directly from the data line ("parasite power"), eliminating the need for an external power supply.

Conventionally, most of the commercially available blood gas analyzers house the electrodes in an aluminum chassis, with heater circuit and maintained at 37° C. In addition to that the sample solution is preheated to 37° C. prior to introducing the sample solution in the electrode train for measurement. In contrast, the reference housing 800 in communication with the computing device may be configured to accurately calculate the temperature coefficient for pH and also for the $HCO_3$ measurements, and incorporating them in the algorithm of Equation 1, thereby saving the heated aluminum chassis and also preheating of the sample solution. This in turn enhances the life of the electrodes, and reduces the maintenance of the analyzer such as the reference housing 800. Further the analyzer, either operating standalone or in combination with the computing device, may read the temperature of the electrode train every time it takes the measurements of sample solution mV, and one point calibration mV. The analyzer or the computing device may accordingly report the result at 37° C. as required.

Other embodiments of the present invention will be apparent to those skilled in the art after considering this disclosure or practicing the disclosed invention. The specification and examples above are exemplary only.

While several variations of the present invention have been illustrated by way of example in preferred or particular embodiments, it is apparent that further embodiments could be developed within the spirit and scope of the present invention, or the inventive concept thereof. However, it is to be expressly understood that such modifications and adaptations are within the spirit and scope of the present invention, and are inclusive, but not limited to the following appended claims as set Those skilled in the art will readily observe that numerous modifications, applications and alterations of the device and method may be made while retaining the teachings of the present invention.

We claim the following invention:

1. A differential-type carbon dioxide sensor comprising:
a pH electrode having a pH-sensitive membrane;
a bicarbonate electrode having a bicarbonate-sensitive membrane;
a chloride electrode having a membrane with no selectivity towards bicarbonate and towards salicylate being within a predetermined therapeutic range, wherein the pH electrode, the bicarbonate electrode, and the chloride electrode operate in tandem with each other; and
a reference electrode being enclosed in a chamber;
wherein each of the pH electrode, bicarbonate electrode, and chloride electrode comprise:
a base;
a cavity formed within the base, the cavity containing a fluid and an electrode membrane;
an inlet lumen providing fluid communication through the base to the cavity;
an outlet lumen providing fluid communication through the base to the cavity;
wherein the inlet lumen and the outlet lumen defining a fluid flow path.

2. The differential-type carbon dioxide sensor of claim 1, wherein the membranes of each of the pH electrode, bicarbonate electrode, and chloride electrode define a tubular flow path portion of the fluid flow path within each electrode.

3. The differential-type carbon dioxide sensor of claim 1 wherein the fluid contained in each of the electrode cavities is a buffered solution.

4. The differential-type carbon dioxide sensor of claim 1, wherein the bicarbonate electrode is filled with a buffered internal filling solution.

5. The differential-type carbon dioxide sensor of claim 1, wherein the chloride electrode is filled with an unbuffered internal filling solution.

6. The differential-type carbon dioxide sensor of claim 1, wherein the membrane of the chloride electrode comprises approximately 65% by weight of a lipophilic additive and approximately 35% by weight of a polymer matrix.

7. The differential-type carbon dioxide sensor of claim 1, wherein a measurement performed using the pH-sensitive membrane is independent of a measurement performed using the bicarbonate-sensitive membrane and a measurement performed using the membrane of the chloride electrode.

8. The differential-type carbon dioxide sensor of claim 1, wherein the electrodes are arranged along an electrode train having one electrode next to another along a sample flow path.

9. The differential-type carbon dioxide sensor of claim 1 further comprising a computer configured to calibrate each of the pH electrode, bicarbonate electrode, and chloride electrode.

* * * * *